United States Patent [19]
Van Iten

[11] Patent Number: 5,542,914
[45] Date of Patent: Aug. 6, 1996

[54] ENCAPSULATED TAMPON WITH AN APPLICATOR

[75] Inventor: Thomas P. Van Iten, Neenah, Wis.

[73] Assignee: Kimberly-Clark Corporation, Neenah, Wis.

[21] Appl. No.: 364,838

[22] Filed: Dec. 27, 1994

Related U.S. Application Data

[63] Continuation of Ser. No. 192,203, Feb. 2, 1994, abandoned, which is a continuation of Ser. No. 16,626, Feb. 12, 1993, abandoned.

[51] Int. Cl.$^6$ ................................. A61F 13/20; A61F 13/15
[52] U.S. Cl. ............................. 604/11; 604/363; 604/374; 604/904
[58] Field of Search .................................. 604/59, 11–18, 604/285–288, 358, 363, 385.1, 374, 904

[56] References Cited

U.S. PATENT DOCUMENTS

| | | | |
|---|---|---|---|
| 639,864 | 12/1899 | Von Raitz . | |
| 684,085 | 10/1901 | Murphy | 604/287 |
| 726,460 | 4/1903 | Reid | 604/15 |
| 749,220 | 1/1904 | Pond . | |
| 812,769 | 2/1906 | Pond | 604/387 |
| 812,770 | 2/1906 | Pond | 604/387 |
| 1,575,123 | 3/1926 | Martocci-Pisculli . | |
| 1,582,201 | 4/1926 | Whittaker . | |
| 1,794,221 | 2/1931 | Washburn et al. | 604/15 |
| 2,267,030 | 12/1941 | Hill | 128/285 |
| 2,298,752 | 10/1942 | Crockford | 604/11 |
| 2,330,257 | 9/1943 | Bailey | 18/55 |
| 2,340,311 | 2/1944 | Donovan | 128/285 |
| 2,351,836 | 6/1944 | Popper | 604/16 |
| 2,440,141 | 4/1948 | Donovan | 128/285 |
| 2,476,956 | 7/1949 | Bonham | 604/15 |
| 2,499,414 | 3/1950 | Rabell | 128/285 |
| 2,501,972 | 3/1950 | Seidler | 604/15 |
| 2,519,912 | 8/1950 | Luan | 604/11 |
| 3,572,341 | 3/1971 | Glassman | 128/285 |
| 3,618,605 | 11/1971 | Glassman | 128/270 |
| 3,791,385 | 2/1974 | Davis et al. | 128/263 |
| 3,794,024 | 2/1974 | Kokx et al. | 128/285 |
| 3,794,029 | 2/1974 | Dulle | 128/285 |
| 3,805,785 | 4/1974 | Marginet | 604/12 |
| 3,834,389 | 9/1974 | Dulle | 128/285 |
| 3,841,333 | 10/1974 | Zalucki | 128/285 |
| 3,965,905 | 6/1976 | Schoenholz et al. | 128/285 |
| 3,983,875 | 10/1976 | Truman | 604/11 |
| 4,077,408 | 3/1978 | Murray et al. | 128/285 |
| 4,077,409 | 3/1978 | Murray et al. | 604/904 |
| 4,269,187 | 5/1981 | Sukurai et al. | 604/904 |
| 4,335,720 | 6/1982 | Glassman | 128/270 |
| 4,421,504 | 12/1983 | Kline | 604/12 |
| 4,553,965 | 11/1985 | Conn et al. | 604/904 |

FOREIGN PATENT DOCUMENTS

| | | | |
|---|---|---|---|
| 0022704 | 12/1910 | United Kingdom | 604/15 |
| 1582201 | 4/1926 | United Kingdom . | |
| 1462071 | 1/1977 | United Kingdom . | |

*Primary Examiner*—Mary Beth Jones
*Assistant Examiner*—K. M. Reichle
*Attorney, Agent, or Firm*—Thomas J. Connelly

[57] ABSTRACT

An encapsulated catamenial tampon is disclosed which can easily and comfortably be inserted into a woman's vagina. The tampon includes an absorbent having a withdrawal string attached thereto. The absorbent is retained in a dissolvable capsule having a cylindrically-shaped base member and a semi-spherically shaped cap member. The base member houses at least a portion of the absorbent and contains a first end and a second end. The first end is completely open while the second end has an opening formed there in through which the withdrawal string passes. The cap member slightly overlaps the first end of the base member to enclose the absorbent. Both the base and cap members have a plurality of openings formed therethrough which decrease the surface area of the capsule to allow the capsule to dissolve quickly.

8 Claims, 3 Drawing Sheets

5,542,914

ENCAPSULATED TAMPON WITH AN APPLICATOR

This is a file wrapper continuation of U.S. Ser. No. 08/192,203 filed Feb. 2, 1994, now abandoned, which is a file wrapper continuation of U.S. Ser. No. 08/016,626 filed Feb. 12, 1993, now abandoned.

FIELD OF INVENTION

This invention relates to a catamenial tampon encapsulated in a dissolvable capsule. The tampon itself is constructed of a plurality of compressed absorbent cones nested together and attached together by a withdrawal string. An alternative embodiment includes an applicator tube for facilitating insertion of the capsule into a body cavity.

BACKGROUND OF THE INVENTION

There are two basic types of tampons used for feminine hygiene. The first type is a digital tampon which is designed to be inserted directly by the user's fingers. The second type is a tampon with an applicator. The applicator can be either a stick or tube which is removably attached to an end of the tampon or a hollow telescoping device which surrounds the tampon. The applicator provides a comfortable method for positioning the tampon into the vagina.

Both types of tampons usually require that the insertion end of the tampon be round or semi-spherical in shape so as to facilitate the insertion process. A tampon having a flat end or a concave shape, such as the base end of a cone, can cause a great amount of discomfort while being inserted. One way to avoid this discomfort is to encapsulate the tampon in a dissolvable capsule. U.S. Pat. Nos. 639,864; 749,220; 1,575,123; 1,582,201 and 2,267,030 teach various forms of medical tampons housed in some sort of capsule. However, none of these patents address the issue of shortening the time period which it takes the capsule to dissolve within the vagina. Another way to ease the insertion of the tampon into the vagina is to coat the forward end of the tampon. This has been taught in U.S. Pat. Nos. 2,340,311 and 2,440141.

Presently, most tampons utilize a single cylindrically shaped pledget with a round convex tip. These tampons have a predetermined amount of absorbent capacity. It has found that by constructing a tampon out of a plurality of individual, compressed absorbent cones, the absorption capacity of a tampon can be significantly increased. The use of one or more absorbent cones has been taught in the following U.S. Pat. Nos.: 2,330,257; 2,499,414; 3,572,341; 3,618,605; 3,794,024; 3,834,389; 3,794,029 and 4,335,720. However, none of these patents teach the use of several compressed absorbent cones nor the combination of such absorbent cones enclosed in a dissolvable capsule. A patent which teaches the use of multiple flat absorbent elements is found in U.S. Pat. No. 3,965,905. Likewise, U.S. Pat. No. 3,841,333, although not teaching a tampon, does teach a menses collector having several superposed rows of collecting cups.

Now a catamenial tampon has been invented which consists of a plurality of compressed absorbent cones attached together to provide increased absorbent capacity. This absorbent is encapsulated in a unique capsule which has been designed to dissolve quickly when positioned within a woman's vagina.

SUMMARY OF THE INVENTION

Briefly, this invention relates to an encapsulated catamenial tampon which is constructed of an absorbent and having a withdrawal string attached thereto. The tampon is enclosed in a dissolvable capsule which provides an easy and comfortable means for inserting the tampon in a body cavity, such as the vagina. The capsule is capable of being dissolved by the interaction of heat, moisture and/or body fluid. The capsule contains a cylindrically shaped base member and a semi-spherically shaped cap member. The base member houses at least a portion of the absorbent and has a first end and a second end. The first end is completely open and the second end has an opening formed there in through which the withdrawal string passes. The cap member slightly overlaps the base member so as to enclose the absorbent. Both the base and cap members contain a plurality of openings formed therethrough which decrease the surface area of the capsule to allow the capsule to dissolve quickly.

The general object of this invention is to provide an encapsulated catamenial tampon. A more specific object of this invention is to provide an encapsulated catamenial tampon which allows for easy and comfortable insertion of a tampon into a body cavity.

Another object of this invention is to provide an encapsulated catamenial tampon with a removable applicator tube for facilitating insertion of the encapsulated tampon into a woman's vagina.

A further object of this invention is to provide a convenient and safe means for inserting a tampon, which does not have a rounded tip, into a woman's vagina.

Still another object of this invention is to provide an inexpensive means for inserting a tampon into a body cavity without the danger of abrading delicate vaginal tissues.

Still further, an object of this invention is to provide an encapsulated catamenial tampon which can quickly dissolve within a woman's vagina by the interaction of body heat, moisture and/or body fluid.

Other objects and advantages of the present invention will become more apparent to those skilled in the art in view of the following description and the accompanying drawings.

DETAILED DESCRIPTION OF THE PREFERRED EMBODIMENTS

Figure 1:
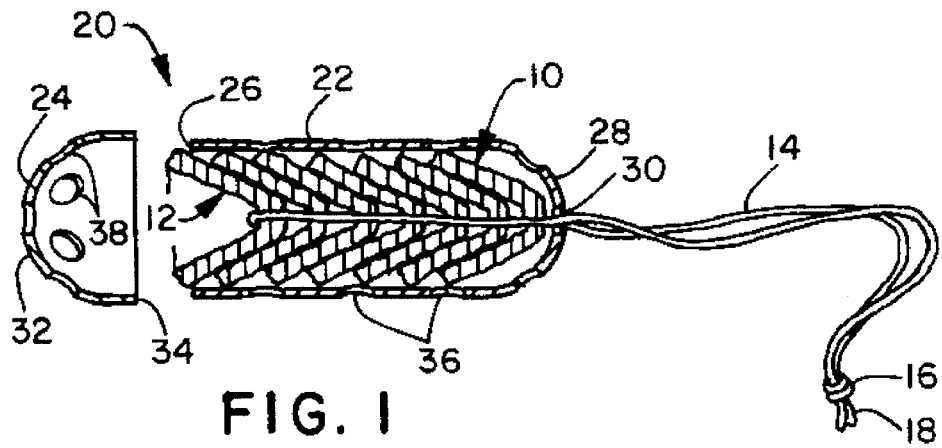
FIG. 1 is an exploded cross-sectional view of a catamenial tampon housed in a capsule having a plurality of openings uniformly distributed about the outer periphery of the capsule.

Referring to FIG. 1, a catamenial tampon 10 is shown for the absorption and retention of menstrual fluid. The tampon 10 includes an absorbent 12 having an attached withdrawal string 14. The withdrawal string 14 provides a means for withdrawing the tampon 10 from a woman's vagina after it has absorbed menstrual fluid. The withdrawal string 14 contains a knot 16 formed adjacent to it's free end 18. The knot 16 assures that the withdrawal string 14 does not separate from the absorbent 12.

The absorbent 12 is encapsulated in a smooth, semi-rigid capsule 20 which is capable of being dissolved by exposure to temperature, for example body heat. A temperature above 98° F. should be sufficient to dissolve the capsule. The capsule 20 can also be dissolved by being exposed to moisture or by being brought into contact with certain body fluid. The combination of two or more of these conditions can shorten the time period required to dissolve the capsule 20. The capsule 20 is made of a soluble gelatinous substance or like material which is similar to those capsules which are currently sold to orally dispense drugs and medication into a human body. A suitable wall thickness for the capsule 20 is in the range of about 0.007 inches to about 0.011 inches (about 0.177 mm to about 0.279 mm).

The capsule 20 contains two members, a base member 22 and a cap member 24. The base member 22 is cylindrically-shaped and is sized to enable it to enclose a major portion of the absorbent 12. The base member 22 has a first end 26 and a second end 28. The first end 26 is completely open to permit the absorbent 12 to be easily inserted into it while the second end 28 has a central opening 30 formed therein through which the withdrawal string 14 passes. The central opening 30 can be in the range of 0.032 to about 0.062 inches (0.812 mm to about 1.58 mm). The cap member 24 has a semi-spherically-shaped first end 32 and a second end 34 which is completely open. The cap member 24 is shorter in length than the base member 22 and has an internal diameter which is slightly larger than the exterior diameter of the base member 22. The difference in diameters enable the cap member 24 to slightly overlaps the base member 22 and enclose the remaining portion of the absorbent 12. It is important to obtain a snug fit between the cap member 24 and the base member 22 so as to prevent the two members from becoming separated.

The cap member 24 should not overlap a significant portion of the base member 22 because this could prolong the time it takes for that part of the base member 22 to dissolve. One of the important features of this invention is that the capsule 20 should totally dissolve very quickly. In actual use, it is contemplated that the capsule 20 will dissolve in less than a minute, preferably in less than 45 seconds, more preferably, in less than 30 seconds, and most preferably, within 15–25 seconds. The actual amount of time that it will take a capsule to dissolve will depend upon a number of factors. The size of the capsule is one factor. For example, if the capsule encloses a regular size tampon, it is more likely to dissolve faster than if the capsule enclosed a larger, super size tampon. The body temperature of the user, the exact position of the capsule 20 within the vagina, the thickness of the gelatin skin of the capsule, the composition of the capsule, the size and number of openings formed in the periphery of the capsule, etc. will all influence how fast the capsule will dissolve.

It has been found that the physical appearance of the capsule 20 can be altered to enable it to dissolve quickly. One way to accomplish this is to form a plurality of openings 36 and 38 in the base and cap members, 22 and 24 respectively. The openings 36 and 38 can pass completely through the capsule 20 or be only indentations formed in the outer peripheral surface of the capsule 20 depending upon one's wishes. Preferably, the openings 36 and 38 will pass completely through the thickness of both the base and cap members, 22 and 24 respectively. In either case, the openings 36 and 38 serve to decrease the surface area and/or the thickness of the capsule 20 and therefore decrease the amount of gelatin which has to dissolve. By forming the openings 36 and 38 in the capsule 20, there is less capsule material to dissolve and the body fluid can instantaneously be absorbed by the absorbent 12. As the absorbent 12 expands it will assist in the destruction and dissolving of the capsule 20. It is possible to size the openings 36 and 38 such that the rate of dissolving can be controlled. This is advantageous when one desires to fabricate a capsule wherein the cap member 24 dissolves before the base member 22 or vice versa.

The openings 36 and 38 can be randomly or uniformly arranged about the periphery of the capsule 20. It is also possible to make the openings 36 and 38 of different sizes and shapes. The size of each opening should not be so large as to allow the absorbent 12 to extend out of the capsule 20 or be so small that they do not permit the capsule 20 to dissolve quickly. The shape of the openings 36 and 38 can be circular, ovate, slotted, rectangular, oval, elongated slits, or any other shape which one desires. It is possible to size the openings 36 in the base member 22 to be different in size and/or quantity then the openings in the cap member 24.

Figure 2:
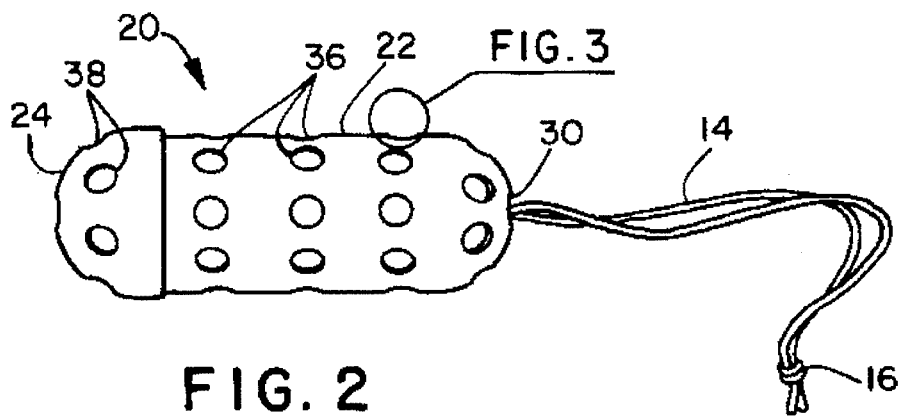
FIG. 2 is a plan view of an encapsulated catamenial tampon having a plurality of openings randomly arranged in the capsule.
Figure 3:
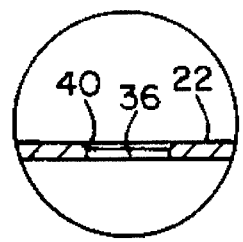
FIG. 3 is an enlarged view of one of the openings having a chamfered edge which is formed in the capsule depicted in FIG. 2.

Referring to FIGS. 2 and 3, a capsule 20 is shown with circular openings 36 formed in the base member 22 and similar size circular openings 38 formed in the cap member 24. The area of all of the openings 36 and 38 can represent from between about 10% to about 50% of the total surface area of the capsule 20. In FIG. 3, one can see that the periphery of each opening 36 contains a chamfer or bevel 40. The periphery of each opening 38 can also contain a chamfer or bevel 40 to minimize pinching vaginal tissue when the capsule 20 is inserted into a woman's vagina. The chamfer or bevel 40 also serves two further purposes. First, it cuts the edge off of the material surrounding each opening 36 and therefore make for a smooth surface. Second, it enlarges the outer or exterior portion of each opening 36 and therefore decreases the amount of gelatinous material which has to dissolve once the capsule 20 is inserted into the woman's vagina. It is important to note that the openings 36 and 38 should not be formed of such a size or shape, nor be arranged on the periphery of the capsule 20, such that they cause the inner tissues of the vagina to be pinched or cut when the capsule 20 is being inserted or before it totally dissolves.

Figure 4:
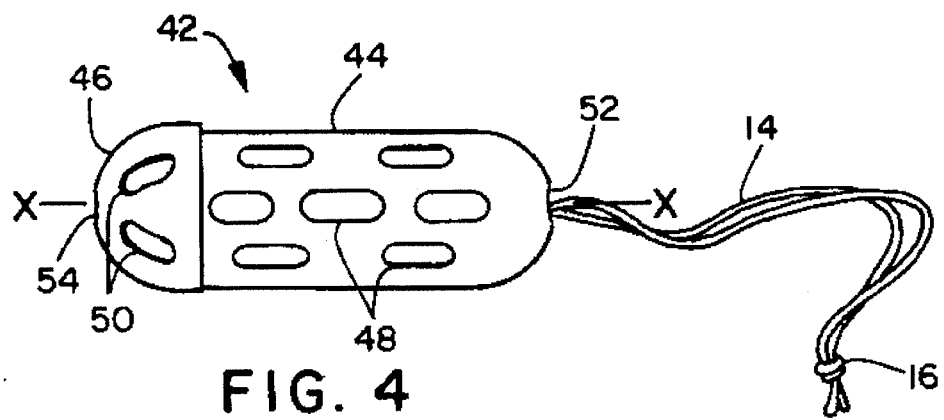
FIG. 4 is a plan view of an encapsulated catamenial tampon having a plurality of slots randomly arranged in the capsule.

Referring to FIG. 4, an alternative embodiment of a capsule 42 is shown containing a base member 44 and a cap member 46. A plurality of longitudinal slots, 48 and 50, are formed in the base and cap members, 44 and 46 respectively. The slots 48 and 50 are arranged so that the longitudinal axis of each slot is aligned parallel to the longitudinal central axis X—X of the capsule 42. This arrangement allows the capsule 42 to have the required structural integrity to be inserted into a woman's vagina without breaking apart or becoming distorted. The capsule 42 also contains a central opening 52 formed in the base member 44 through which the withdrawal string 14 passes and a central opening 54 formed at the apex of the semi-spherical cap member 46 which can assist the tip of the cap member 46 in dissolving rapidly. The central openings 52 and 54 can be in the range of 0.032 to about 0.062 inches (0.812 mm to about 1.58 mm).

Figures 5, 6:
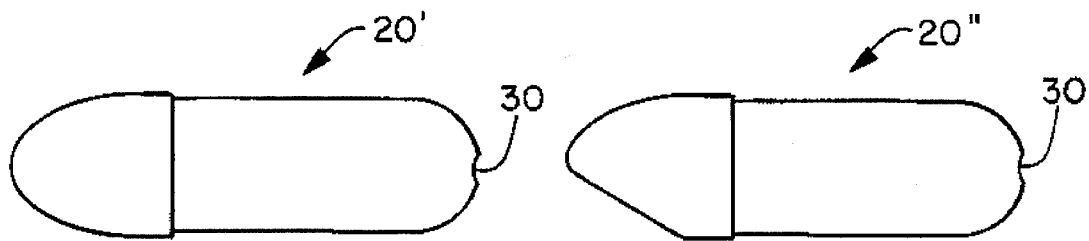
FIG. 5 is a plan view of a capsule having an ellipsoidal-shape with a plurality of openings formed therein omitted for clarity.
FIG. 6 is a plan view of a capsule having a lipstick-shape with a plurality of openings formed therein omitted for clarity.

Referring to FIGS. 5 and 6, two additional capsules 20' and 20" are shown having different shaped tips. In FIG. 5, the capsule 20' has an ellipsoidal-shaped tip, while in FIG. 6, the capsule 20" has a lipstick-shaped tip. It should be noted that both of these capsules would also contain a plurality of openings formed along their length and about their circumference but that such openings have been omitted to better illustrate the shape of the insertion end.

Figure 7:
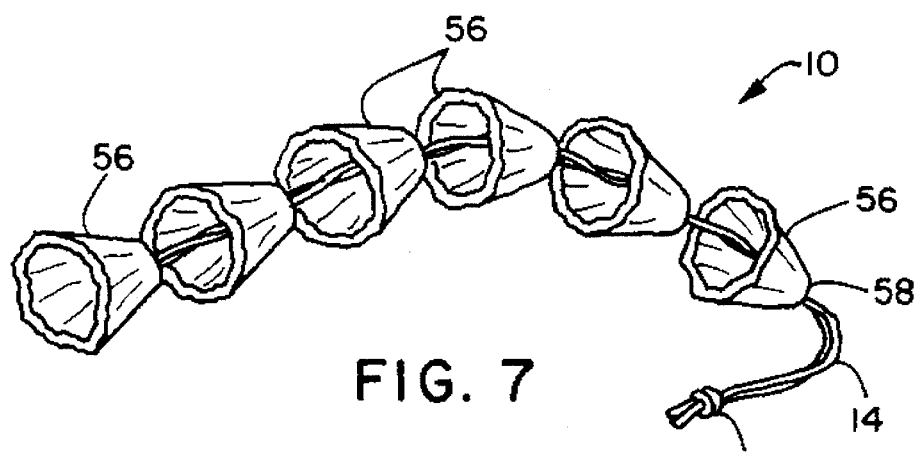
FIG. 7 is an exploded view of a tampon constructed from a plurality of compressed absorbent cones which are attached together at their apex by a withdrawal string.
Figure 8:
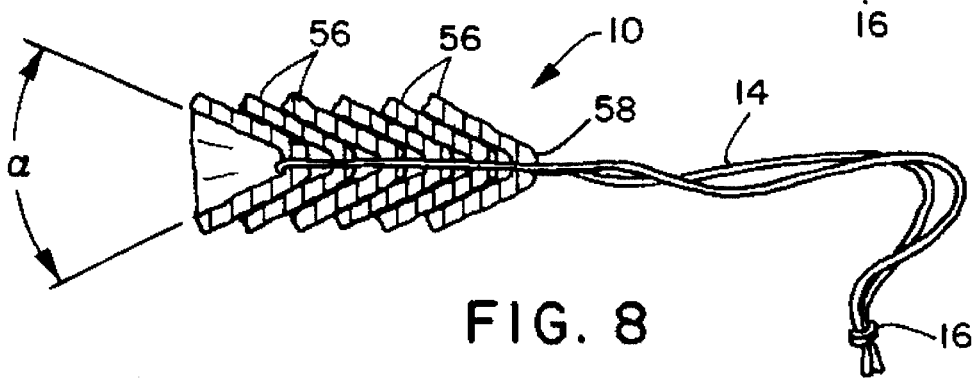
FIG. 8 is a cross-section view of a tampon constructed from a plurality of compressed absorbent cones having an included angle of less than 60°.

Referring to FIGS. 7 and 8, the tampon 10 is constructed from a plurality of compressed layers of fibrous absorbent material formed into hollow cones 56. In FIG. 7, the cones 56 are shown slightly separated only for the purpose of illustration. The base of each cone 56 faces the insertion end of the tampon and the apex of each cone 56 faces toward the trailing or second end of the base member of the capsule 20. This orientation facilitates removal of the tampon 10 from the vagina. Each cone 56 is capable of expanding and swelling as it absorbs body fluid. The absorbent material can be made of cotton, wool, sponge, highly absorbent cellulose fibers, coform, cotton-rayon blends or combinations thereof. Each absorbent cone 56 is formed from a disc of material having a diameter of between about 0.5 to about 1.5 inches (about 12.7 mm to about 38.1 mm). A preferred diameter is about 0.625 to about 0.75 inches (about 15.8 mm to about 19.05 mm). The initial disc diameter which one chooses will be dictated by the size of the finished tampon one desires.

Each cone 56 has exterior sides which slope toward the apex and form an included angle alpha of between about 30° to about 60°. The length of each cone 56 is determined by it's diameter and the angular slope of it's sides. In FIGS. 7 and 8, the diameter and length of each cone 56 is identical. The wall thickness of each cone 56 ranges from between about 0.062 to about 0.125 inches (about 1.58 mm to about 3.17 mm). The inside radius, as measured at the apex of each cone 56, should be in the range of about 0.062 to about 0.187 inches (about 1.58 mm to about 4.76 mm).

As the absorbent disc is compressed, it is also pierced to provide an opening 58 approximate the apex of each cone 56. The openings 58 provide a means for threading or sewing the looped withdrawal string 14 through the cones 56. This provides a means for easily removing the tampon from the vagina once it has absorbed a sufficient quantity of menstrual fluid.

The number of cones 56 which are nested or stacked together to form the tampon 10 can vary depending upon the length of tampon one desires, the absorbent capacity required, etc. Five to twelve cones 56 can form such a tampon, with 6 to 9 cones being preferred. Tampons are currently sold in various sizes denotes as slender, regular and super. Typically, a tampon will have a length of between about 1.5 to about 2.5 inches (about 38.1 mm to about 63.5 mm) with a length of approximately 2 inches (about 50.8 mm) being standard. The tampon should have an absorbent capacity of at least 0.75 grams of body fluid.

Figure 9:
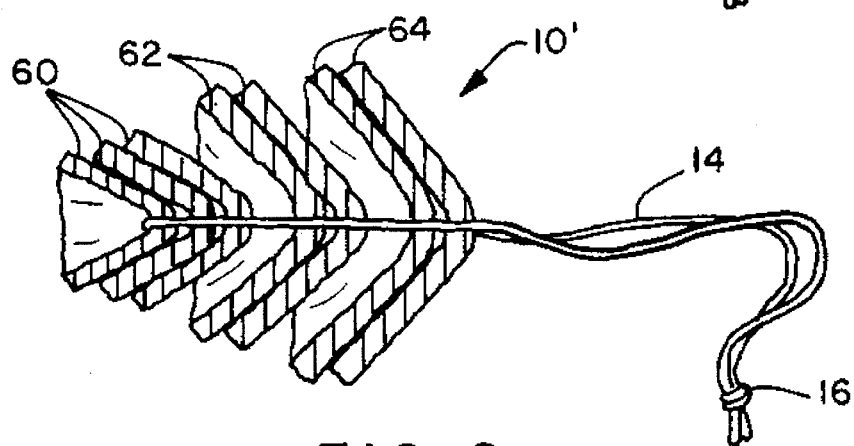
FIG. 9 is a cross-section view of an alternate embodiment of a tampon constructed from a plurality of compressed absorbent cones, wherein some of the cones have different diameters.

Referring to FIG. 9, a tampon 10' is depicted constructed of three different size absorbent cones 60, 62 and 64. The cones 60, 62 and 64 are shown slightly separated only for the purpose of illustration. The smallest diameter cones 60 are formed from compressed disc having a diameter of about 0.75 inches (about 19.05 mm). The intermediate size cones 62 are formed from absorbent disc having a diameter of about 1 inch (25.4 mm), while the largest cones 64 are formed from absorbent disc having a diameter of about 1.25 inches (31.8 mm). Besides the difference in size, the cones 60, 62 and 64 can vary in fiber makeup. For example, the small cones 60 can be formed from a blend of about 60% rayon fibers and 40% cotton inter. Rayon fibers of 3 denier, with a dull finish, high crimp and having a staple length of about 1.5 inches (38.1 mm) works well. The cotton linter should be bleached and be the second cut. The intermediate size cones 62 can consist of 50% rayon fibers and 50% cotton linter. The large size cones 64 can consist of 60% rayon fibers and 40% cotton linter. This arrangement will allow the intermediate and larger size cones, 62 and 64 respectively, to expand quicker and be more resilient than the smaller size cones 60. The reason for this is that the cotton linter absorb the body fluid while the rayon fibers provide the resilient feature. The higher the percent of rayon fibers, the more the cone can expand. It should be noted that the number of cones as well as the composition of each cone can be varied to meet one's particular needs.

Figure 10:
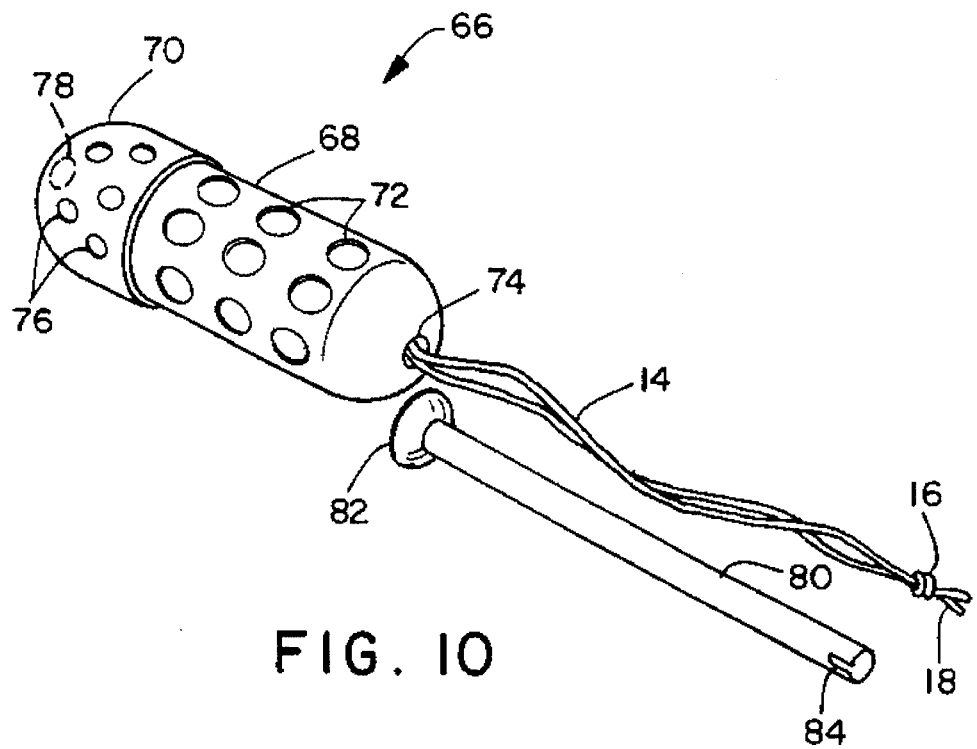
FIG. 10 is an exploded view of an encapsulated catamenial tampon with an applicator tube for facilitating insertion of the capsule into a woman's vagina.
Figure 11:
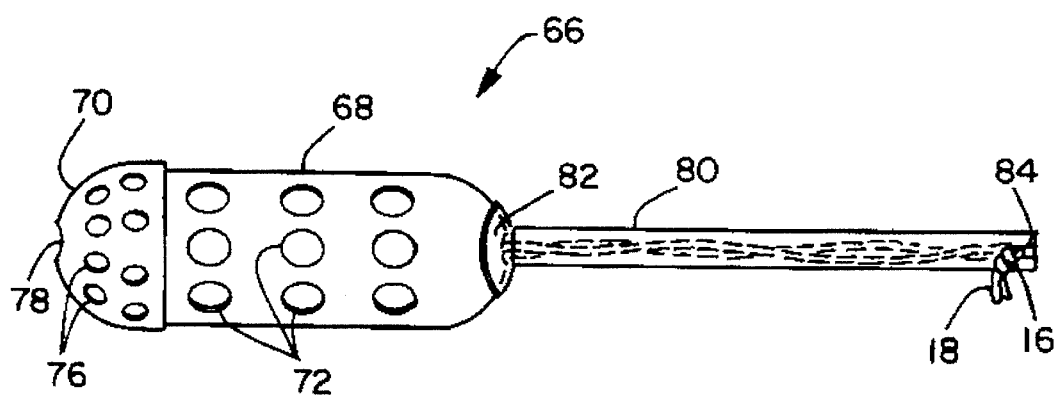
FIG. 11 is a side view of the assembled tampon capsule and applicator tube shown in FIG. 10.

Referring to FIGS. 10 and 11, a capsule 66 is shown which includes a base member 68 and a cap member 70. The base member has a plurality of openings 72 formed along it's length which extend around it's circumference and an axial opening 74, through which a withdrawal string 14 passes. The withdrawal string 14 has a knot 16 formed adjacent to it's free end 18. The cap member 70 is shorter in length than the base member 68 and has a plurality of openings 76 formed in it's periphery. The openings 76 are smaller in size and number than the openings 72 formed in the base member so as to facilitate a smooth and comfortable insertion of the capsule 66 into a woman's vagina. The cap member 70 also contains an axial opening 78 located approximate it's tip. The axial opening 78 permits body fluid to immediately enter into the tampon even before the gelatinous capsule 66 starts to dissolve.

The capsule 66 has a hollow elongated applicator tube 80 attached to the base member 68 which facilitates placement of the capsule 66 into a woman's vagina. The applicator tube 80 can be constructed out of a soft plastic or plastic-like material and has a cup-shaped flange 82 formed on one end which is designed to contact and mate with the outer configuration of the base member 68. The opposite end of the tube 80 has a notch 84 formed therein which is aligned parallel to the longitudinal axis of the tube 80. The notch 84 is sized and configured to receive and retain the withdrawal string 14 such that the knot 16 is positioned adjacent to the exterior surface of the tube 80. The length of the tube 80 is sized to match the length of the withdrawal string 14 so that when the withdrawal string 14 is inserted through the opening in the tube 80 and the notch 84, the knot is positioned adjacent to an exterior surface of the tube 80 and the tube 80 will be held secure and snug against the capsule 66. A length of about 3 inches 76.2 mm) works well for the applicator tube 80. The applicator tube 80 can be straight or curved and can also contain one or more flat spots formed on it's outer periphery to assist the user obtaining a firm grip.

After the capsule 66 is inserted into the vagina, the user removes the knotted end 16 of the withdrawal string 14 from the notch 84. The applicator tube 80 can be separated from the capsule 66 by allowing the withdrawal string 14 to pass through the center of the hollow tube 80. Once the tube 80 is withdrawn, the withdrawal string 14 will extend downward from the capsule 66 and serve as a means for later removing the tampon from the vagina.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. An encapsulated catamenial tampon with an applicator, said combination consisting of:

a) an absorbent;

b) a withdrawal string attached to said absorbent and having an opposite end with a knot formed therein;

c) a dissolvable capsule enclosing said absorbent and providing means for inserting said absorbent into a body cavity, said capsule having a cylindrically-shaped base member and a semi-spherically-shaped cap member, said base member housing at least a portion of said absorbent and having first and second ends, said first end being completely open and said second end having an opening formed therein through which said withdrawal string passes, said cap member slightly overlapping said base member to enclose said absorbent, and both said base member and said cap member having a plurality of openings formed therethrough which decrease the surface area of said capsule to allow said capsule to dissolve quickly; and d) a single elongated applicator tube having a cup-shaped flange formed on one end which contacts said second end of said base member, said applicator tube being sized relative to a length of said withdrawal string and having an opposite end with a notch formed therein for retention of said withdrawal string when said knot is positioned adjacent to an exterior surface of said tube, said applicator tube being held snug against said capsule to facilitate positioning of said capsule in the body cavity.

2. The combination of claim 1 wherein said applicator tube has a predetermined length and said knot is positioned adjacent to the exterior surface of said applicator tube, said applicator tube being held snugly against said second end of said base member to facilitate positioning of said capsule in the body cavity and said withdrawal string being removed from said notch to permit said applicator tube to be withdrawn from the body cavity.

3. The combination of claim 2 wherein said applicator tube has predetermined length of about 3 inches.

4. The combination of claim 1 wherein said second end of said base member has a semi-spherical shape and said cup-shaped flange on said applicator tube has a surface which mates with said semi-spherical-shape of said base member.

5. The combination of claim 1 wherein said openings formed in said cap member are smaller in size than said openings formed in said base member to facilitate insertion of said capsule into the body cavity.

6. The combination of claim 1 wherein said openings formed in said base member are present in greater quantity than said openings formed in said cap member.

7. The combination of claim 1 wherein said openings formed in both said base and cap members are chamfered to minimize pinching vaginal tissue when said capsule is inserted into a woman's vagina.

8. An encapsulated catamenial tampon with an applicator, said combination consisting of:

a) an absorbent;

b) a withdrawal string attached to said absorbent and having an opposite end with a knot formed therein;

c) a dissolvable capsule enclosing said absorbent and providing means for inserting said absorbent into a body cavity, said capsule having a cylindrically-shaped base member and a lipstick-shaped cap member, said base member housing at least a portion of said absorbent and having first and second ends, said first end being completely open and said second end having an opening formed therein through which said withdrawal string passes, said cap member slightly overlapping said base member to enclose said absorbent, and both said base and cap members having a plurality of openings formed therethrough which decrease the surface area of said capsule to allow said capsule to dissolve quickly; and d) a single elongated applicator tube having a cup-shaped flange formed on one end which contacts said second end of said base member, said applicator tube being sized relative to a length of said withdrawal string and having an opposite end with a notch formed therein for retention of said withdrawal string when said knot is positioned adjacent to an exterior surface of said tube, said applicator tube being held snug against said capsule to facilitate positioning of said capsule in the body cavity.

* * * * *